US009192691B2

(12) United States Patent
Bourne

(10) Patent No.: US 9,192,691 B2
(45) Date of Patent: Nov. 24, 2015

(54) GEL CAN AIR FRESHENER WITH DUAL SCENT

(71) Applicant: American Covers, Inc., Draper, UT (US)

(72) Inventor: Chris Bourne, Standsbury Park, UT (US)

(73) Assignee: American Covers, Inc., Drapper, UT (US)

( * ) Notice: Subject to any disclaimer, the term of this patent is extended or adjusted under 35 U.S.C. 154(b) by 211 days.

(21) Appl. No.: 14/060,169

(22) Filed: Oct. 22, 2013

(65) Prior Publication Data

US 2015/0108243 A1    Apr. 23, 2015

(51) Int. Cl.
*A61L 9/04*       (2006.01)
*A61L 9/12*       (2006.01)
*B65D 43/18*      (2006.01)

(52) U.S. Cl.
CPC ..................... *A61L 9/125* (2013.01)

(58) Field of Classification Search
CPC ........... A61L 9/125; A61L 9/04; A61L 9/048; A61L 9/12; A24F 25/00; B65D 43/18; B65D 43/24
USPC .......... 239/34–60, 6; 220/506, 501, 502, 505; 428/905
See application file for complete search history.

(56) References Cited

U.S. PATENT DOCUMENTS

| | | | | |
|---|---|---|---|---|
| 2,277,377 A | * | 3/1942 | Warner .................... | F24F 6/043 239/45 |
| 3,239,145 A | * | 3/1966 | Russo ....................... | A61L 9/12 206/0.5 |
| D212,753 S | | 11/1968 | Tughan | |
| 3,804,331 A | * | 4/1974 | Levey ....................... | A61L 9/12 239/59 |
| 3,908,906 A | * | 9/1975 | Crowle .................... | A61L 9/12 239/58 |
| D254,930 S | | 5/1980 | Mandon et al. | |
| D254,931 S | | 5/1980 | Mandon et al. | |
| D255,263 S | | 6/1980 | Mandon et al. | |
| 4,280,649 A | | 7/1981 | Montealegre | |
| D268,361 S | | 3/1983 | Von Philipp et al. | |
| D268,520 S | | 4/1983 | LeCaire, Jr. | |
| D268,614 S | | 4/1983 | Von Philipp et al. | |
| 4,382,548 A | | 5/1983 | Van der Heijden | |
| 4,428,892 A | * | 1/1984 | Berliner ................. | G10G 7/005 239/51.5 |
| D272,757 S | | 2/1984 | Fee et al. | |
| 4,549,693 A | * | 10/1985 | Barlics ....................... | A61L 9/12 206/0.5 |
| D289,919 S | | 5/1987 | O'Neil, Jr. | |
| 5,005,763 A | * | 4/1991 | Cullen .................... | B29C 65/08 239/55 |
| 5,139,864 A | * | 8/1992 | Lindauer ................. | A01N 25/18 428/304.4 |
| 5,180,107 A | * | 1/1993 | Lindauer .................... | A61L 9/12 239/35 |
| 5,579,601 A | * | 12/1996 | Norrad ................... | A01M 23/08 43/64 |
| 5,749,519 A | * | 5/1998 | Miller ..................... | A61L 9/127 239/34 |
| D403,420 S | | 12/1998 | Vullion | |
| D403,758 S | | 1/1999 | Bryson et al. | |

(Continued)

*Primary Examiner* — Arthur O Hall
*Assistant Examiner* — Joseph A Greenlund
(74) *Attorney, Agent, or Firm* — Thorpe North & Western, LLP

(57) ABSTRACT

An air freshener comprises a container divided into an inner cylindrical reservoir and an outer annular reservoir with at least two different fragrant materials with different fragrances. A cap is carried by the container and covers the reservoirs. A sleeve extends from the cap into the container between the reservoirs. The cap is movable axially with respect to the container between a raised position in which the at least two different fragrances are released, and a closed position in which the cap covers the container to resist release of the at least two different fragrances.

20 Claims, 7 Drawing Sheets

(56) References Cited

U.S. PATENT DOCUMENTS

| | | | | |
|---|---|---|---|---|
| 5,988,520 A * | 11/1999 | Bitner | ............... | B65F 7/00 220/300 |
| 6,328,935 B1 * | 12/2001 | Buccellato | ............... | A61L 9/03 422/123 |
| 6,592,104 B2 * | 7/2003 | Cox | ............... | A01M 1/2033 261/26 |
| D527,448 S | 8/2006 | Ku | | |
| D550,344 S | 9/2007 | Weggelaar | | |
| D552,724 S | 10/2007 | Chen | | |
| 7,360,671 B2 * | 4/2008 | Slade | ............... | B67D 3/00 137/583 |
| 7,380,370 B2 * | 6/2008 | Livingston | ............... | A01M 29/12 239/47 |
| 7,888,275 B2 * | 2/2011 | Ward | ............... | A61L 9/127 210/505 |
| D640,358 S * | 6/2011 | Irvin | ............... | D23/366 |
| 8,251,299 B1 * | 8/2012 | Irvin | ............... | A61L 9/048 220/23.83 |
| 8,978,999 B2 * | 3/2015 | Lesniak | ............... | A61L 9/12 239/34 |
| 2006/0137241 A1 * | 6/2006 | Yamasaki | ............... | A01M 1/2033 43/125 |
| 2008/0245890 A1 * | 10/2008 | Lockwood | ............... | A01M 1/2055 239/60 |
| 2009/0152374 A1 * | 6/2009 | Litten-Brown | ............... | A61L 9/12 239/60 |
| 2011/0011947 A1 * | 1/2011 | Wallis | ............... | A61L 9/012 239/34 |
| 2011/0288026 A1 * | 11/2011 | Simpson | ............... | A61F 2/08 514/17.2 |
| 2012/0312893 A1 * | 12/2012 | Santini | ............... | A61L 9/035 239/44 |

* cited by examiner

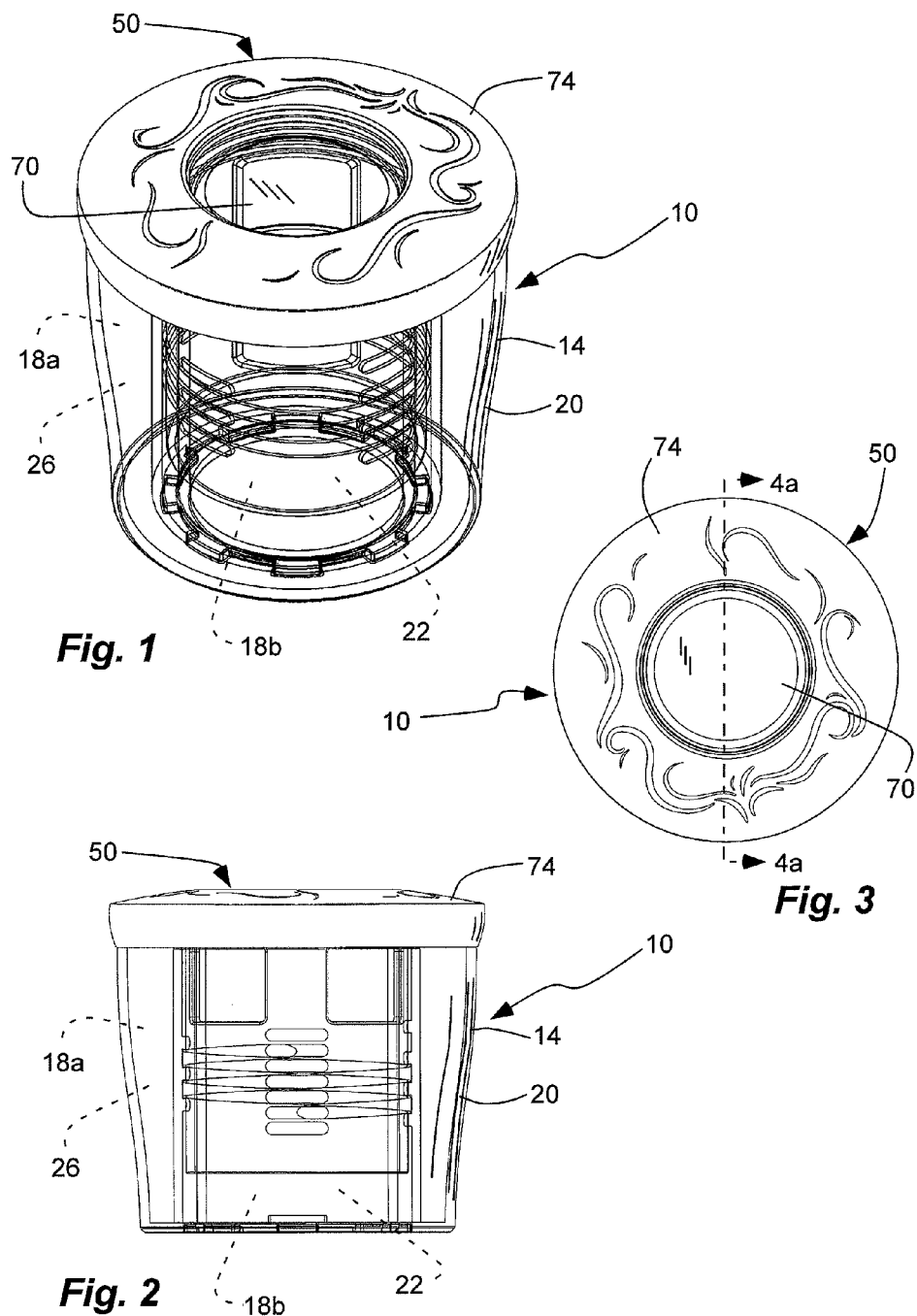

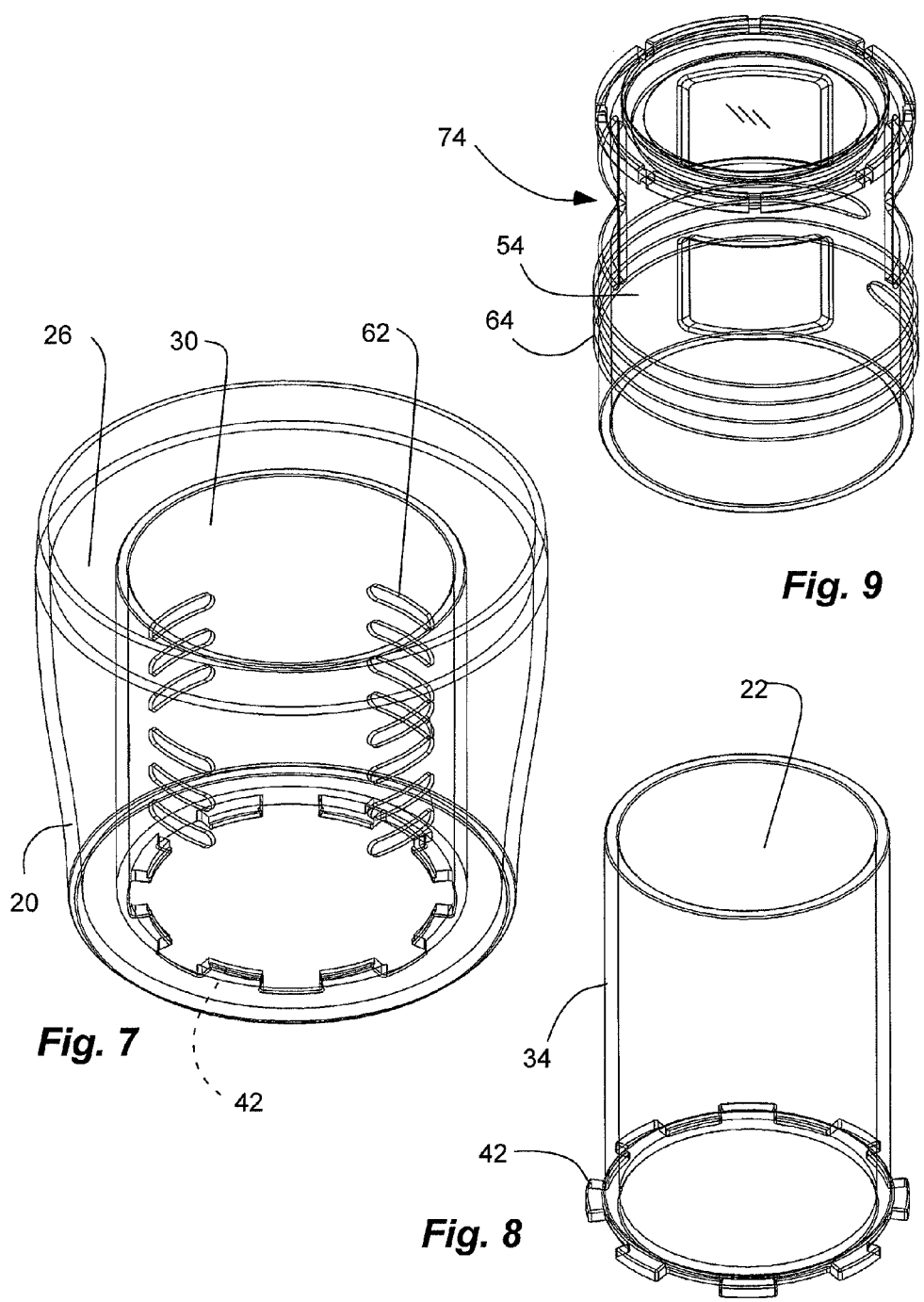

GEL CAN AIR FRESHENER WITH DUAL SCENT

RELATED PATENT(S)/APPLICATION(S)

This is related to U.S. Pat. No. 8,251,299, which is hereby incorporated herein by reference in its entirety.

BACKGROUND

1. Field of the Invention

The present invention relates generally to air fresheners.

2. Related Art Some air fresheners provide a fragrant material in a can with a lid, which when removed allows the fragrance to escape, but also exposes the fragrant material in the entire can to debris, escape, children and/or pets. It will be appreciated the fragrant material can be harmful if ingested and/or a skin or eye irritant. In addition, it will be appreciated that the fragrant material can be harmful to surfaces, such as by staining.

Another air freshener can has a lid with overlapping upward aperture that can turn to align the apertures.

SUMMARY OF THE INVENTION

It has been recognized that it would be advantageous to develop an air freshener to selectively release scent. In addition, it has been recognized that it would be advantageous to develop an air freshener that resists tampering and/or fouling. Furthermore, it has been recognized that it would be advantageous to develop an air freshener to release more than one scent.

The invention provides an air freshener comprising a container divided into an inner cylindrical reservoir and an outer annular reservoir being separate and discrete from, and circumscribing, the inner cylindrical reservoir. At least two different fragrant materials, with different fragrances that permeate over time, are each disposed in a different one of the reservoirs. A cap is carried by the container and covers the reservoirs. A sleeve extends from the cap into the container. The cap is movable axially with respect to the container between a raised position, in which the at least two different fragrances are released, and a closed position, in which the cap covers the container to resist release of the at least two different fragrances.

In addition, the invention provides an air freshener comprising a container and a pair of concentric cylindrical walls disposed in the container, and concentric with one another, and forming an annular gap therebetween, and dividing the container into an inner cylindrical reservoir and an outer annular reservoir circumscribing the inner cylindrical reservoir. A first fragrant material is disposed in the outer annular reservoir from which a first fragrance permeates over time. A second fragrant material is disposed in the inner cylindrical reservoir from which a different second fragrance permeates over time. A cap is carried by the container and covers the reservoirs. A sleeve extends from the cap into the annular gap between the pair of cylindrical walls. At least one opening is in the sleeve. The cap is movable axially with respect to the container between a raised position in which the at least one opening in the sleeve is exposed at least partially to release the second fragrance from the inner cylindrical reservoir through the at least one opening in the sleeve, and the cap is raised to release the first fragrance from the outer annular reservoir, and a closed position in which the at least one opening in the sleeve is disposed in the annular gap and the cap covers the container to resist release of the first and second fragrances.

Furthermore, the invention provides an air freshener comprising an outer annular container having an annular reservoir, and containing a first fragrant material from which a first fragrance permeates over time. The outer annular container has an outer wall and an inner wall. An inner screw thread is formed on the inner wall of the outer annular container. An inner cylindrical container is circumscribed by the outer annular container, and has a cylindrical reservoir containing a second fragrant material from which a different second fragrance permeates over time. The inner cylindrical container has a wall opposing and spaced apart from the inner wall of the outer annular container, and defines an annular gap therebetween. A cap is carried by the container and covers the reservoirs. A cylindrical sleeve extends from the cap into the annular gap between the reservoirs. At least one lateral aperture is in the cylindrical sleeve. An exterior screw thread is formed on the sleeve and engages the interior screw thread on the inner wall of the outer annular container. Rotation of the cap moves the cap axially with respect to the container including a raised position, in which the at least one aperture in the cylindrical sleeve is exposed to release the second fragrance from the inner cylindrical container through the at least one aperture in the sleeve, and the cap is raised to release the first fragrance from the outer annular container, and a closed position in which the at least one aperture in the cylindrical sleeve is disposed in the annular gap and the cap covers the container to resist release of the first and second fragrances.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1 is a perspective view of an air freshener in accordance with an embodiment of the present invention;

FIG. 2 is a top view of the air freshener of FIG. 1;

FIG. 3 is a side view of the air freshener of FIG. 1;

FIG. 7 is a perspective view of an outer annular container of the container of the air freshener of FIG. 1;

FIG. 8 is a perspective view of an inner cylindrical container of the container of the air freshener of FIG. 1;

FIG. 9 is a perspective view of the inverted cup and the sleeve of the cap of the air freshener of FIG. 1, with the outer annular cap removed therefrom;

Figure 4A:
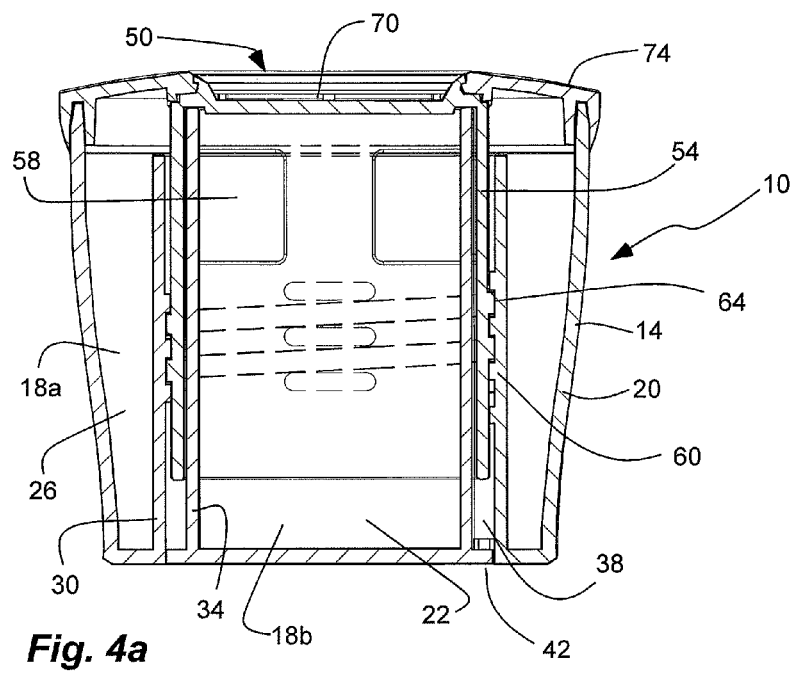
FIG. 4a is a cross-sectional side view of the air freshener of FIG. 1 taken along line 4a of FIG. 3, showing a cap and a sleeve in a closed position with respect to a container.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

As illustrated in FIGS. 1-14, an air freshener device, indicated generally at 10, in an example implementation in accordance with the invention is shown. The air freshener can provide multiple complimentary scented materials in a container with a cap that selectively exposes the scented material or that axially displaces with respect to the container to selectively increase a gap between the cap and the container to control scent release. The air freshener can provide a desired and/or aesthetically pleasing scent, fragrance, aroma or neutralizing agent. Air fresheners are one example of a field that can benefit from the present invention.

The air freshener 10 comprises a container 14 that contains a fragrant material, such as a fragrant gel material, from which a fragrance permeates over time. The container 14 contains at least two different fragrant materials, such as first and second fragrant materials 18a and 18b with different fragrances, such as first and second fragrances. The fragrances can be complimentary. The two fragrances can combine in a synergistic manner with the combined scent being more pleasing or different than either scent individually. The fragrant materials can be separate and discrete with respect to one another in the container. The first fragrant material can be an outer fragrant material, while the second fragrant material can be an inner fragrant material. The fragrant gel material can be a water based gel. In addition, the fragrant material can be transparent or at least translucent. The container 14 can have a cylindrical shape or a cylindrical-shaped perimeter to accommodate rotation as discussed below. In addition, the container 14 can have an outer perimeter wall 20. Furthermore, the container 14 can have a closed bottom and an open upper end or upper opening.

The container 14 can be a divided into separate and discrete containers or reservoirs, including an inner cylindrical reservoir 22 or container, and an outer annular reservoir 26 or container being separate and discrete from, and circumscribing, the inner cylindrical reservoir. The container 14 can be formed by an outer annular container and an inner cylindrical container. Each of the at least two different fragrant materials is disposed in a different one of the reservoirs. The first fragrant material 18a can be disposed in the outer annular reservoir 26 or container, and the second fragrant material 18b can be disposed in the inner cylindrical container 22. Thus, the outer annular container can have the annular reservoir, and can contain the first fragrant material. Similarly, the inner cylindrical container can be circumscribed by the outer annular container, and can have the cylindrical reservoir, and can contain the second fragrant material.

Figure 14:
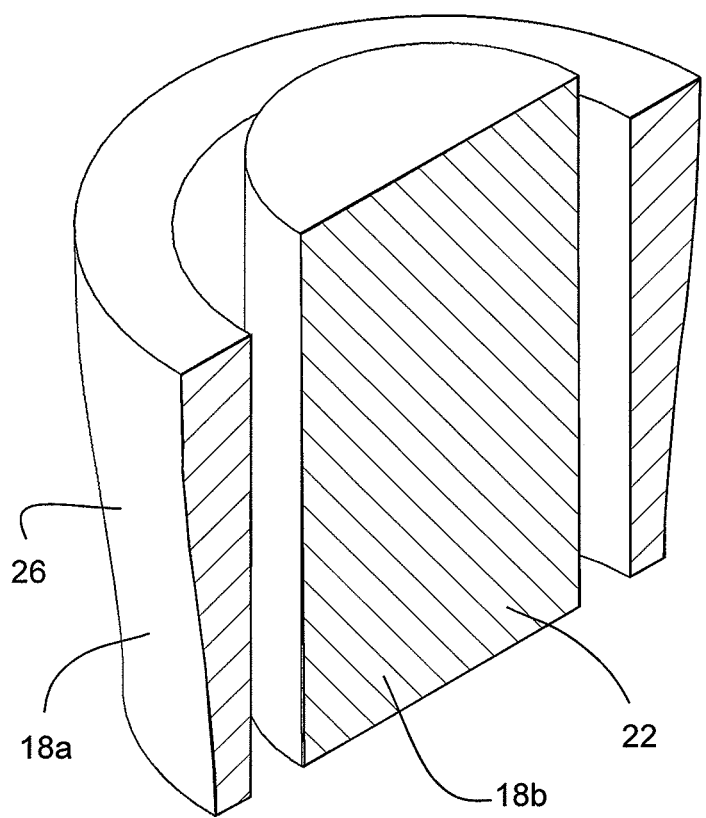
FIG. 14 is a cross-sectional perspective view of volumes defined by the outer annular container and the inner cylindrical container, and/or fragrant material of the containers, of the air freshener of FIG. 1.

As described above, the reservoirs or containers can be separate and discrete, or can have separate and discrete volumes, as shown in FIG. 14. A pair of concentric cylindrical walls 30 and 34 can be disposed in the container 14, and can divide the container into the inner cylindrical reservoir 22 and the outer annular reservoir 26, or the inner cylindrical container 22 and the outer annular container 26. The pair of walls can be vertically oriented and can extend axially or vertically from a bottom wall of the container towards the open upper end of the container. In addition, the pair of walls can be cylindrical to facilitate rotation, as discussed below. Furthermore, the pair of walls can be concentric with one another, and spaced-apart from one another, or can oppose one another, to form an annular gap 38 therebetween. Thus, the outer annular container or reservoir 26 can have or can be formed by an outer wall or outer wall 20 of the container, and an inner wall or outermost wall 30 of the pair of walls. Similarly, the inner cylindrical container or reservoir 22 can have or can be formed by a wall opposing and spaced apart from the inner wall 30 of the outer annular container, or the innermost wall 34 of the pair of walls.

The inner cylindrical container or reservoir 22 and the outer annular container or reservoir 26 can be separately formed. Each of the inner cylindrical container or reservoir 22 and the outer annular container or reservoir 26 can be formed as a single, integral, monolithic piece that is formed together, such as of plastic in an injection molding process. Thus, the inner cylindrical container or reservoir 22 can be formed as a cup with a bottom wall and the opposing wall or innermost wall 34. Similarly, the outer annular container or reservoir 26 can be an annular cup with a bottom wall and the outer wall 20 and inner wall or outermost wall 30. The two containers or reservoirs 22 and 26 can be joined together to form the container 14. For example, an interlocking coupling 42 can be formed between the containers or reservoirs 22 and 26 at a bottom inner rim of the outer annular container or reservoir 26, and at a bottom outer rim of the inner cylindrical container 22. For example, each bottom rim can include a plurality of teeth that intermesh to connect the containers and resist rotation of the containers with respect to one another. The rims or teeth can be adhered together. The bottom walls of the containers can be co-planar or flush with a support surface upon which the container is disposed.

The containers or cups can be formed of, or can include, a material that resists reacting with the fragrant gel material, such as polypropylene. In addition, the container or cups, or walls thereof can be transparent, or at least translucent, so that the fragrant material is visible therethrough. In addition, the fragrant material, or at least the first fragrant material, can be transparent, or at least translucent, so that the second fragrant material is visible therethrough.

Figure 4B:
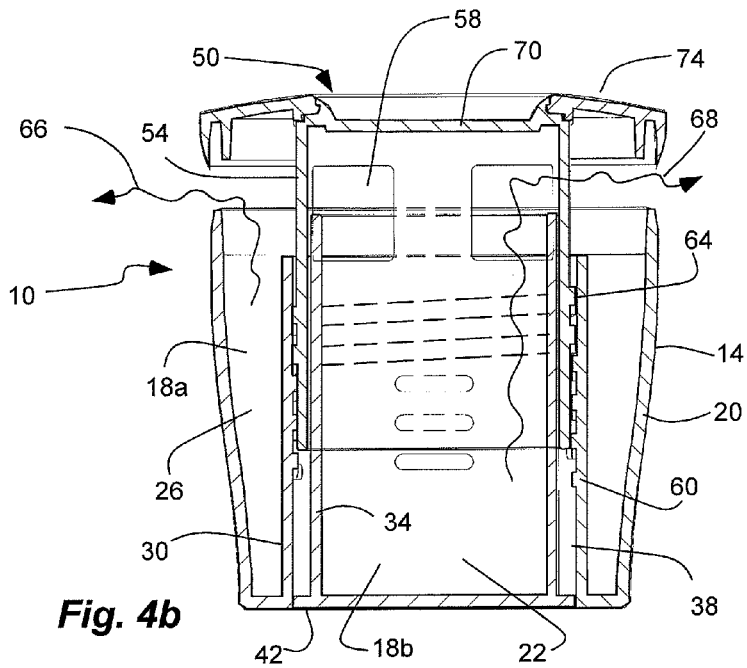
FIG. 4b is a cross-sectional side view of the air freshener of FIG. 1 taken along line 4a of FIG. 3, showing the cap and the sleeve in a raised or open position with respect to the container.
Figure 5:
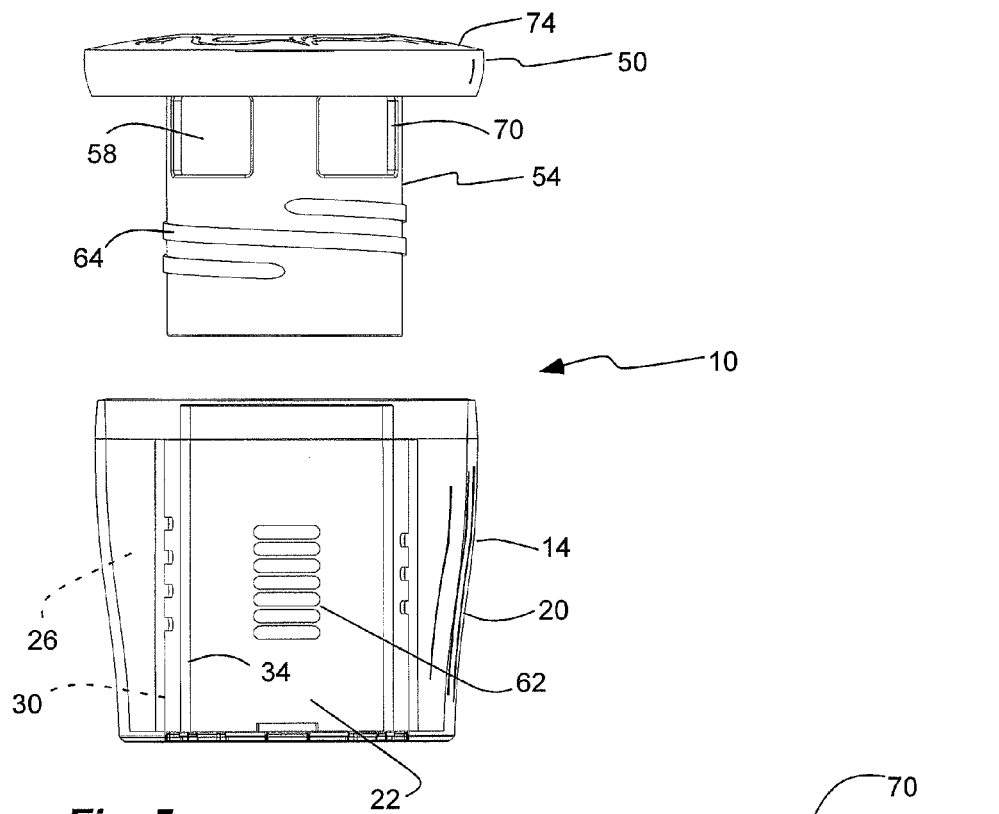
FIG. 5 is an exploded side view of the air freshener of FIG. 1, showing the cap and the sleeve removed from the container.
Figure 6:
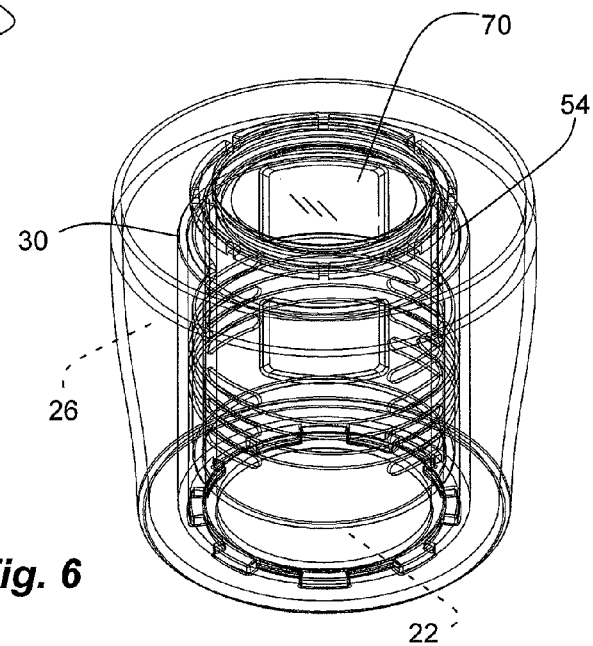
FIG. 6 is a partial perspective view of the air freshener of FIG. 1, showing an outer annular cap removed from an inverted cup and the sleeve to show the inverted cup and the sleeve with respect to the container.
Figure 10:
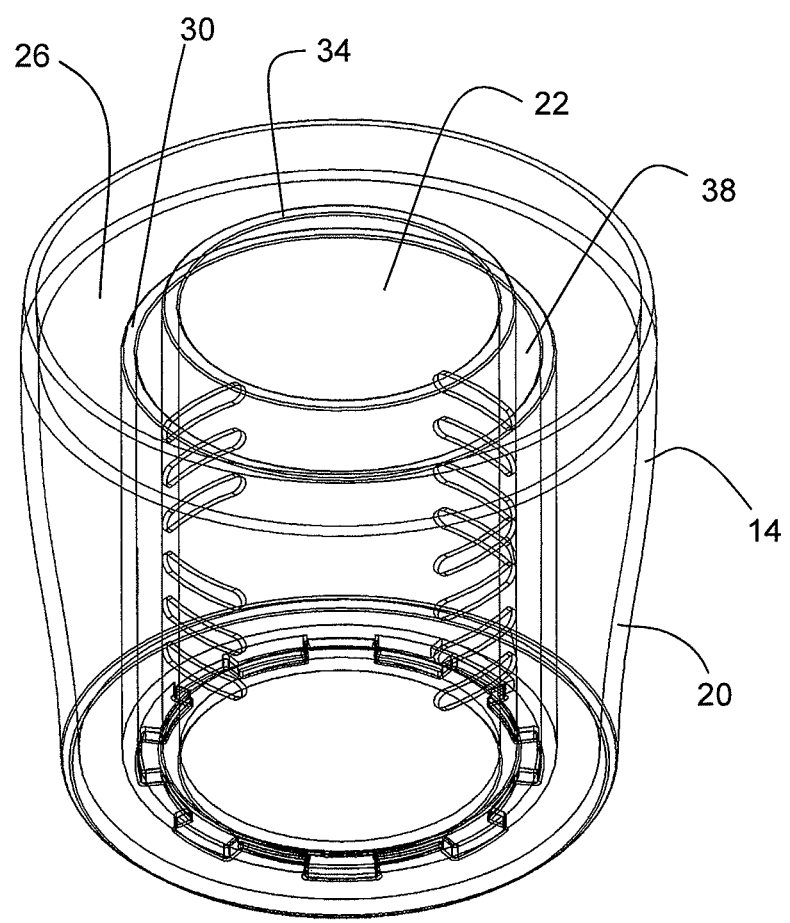
FIG. 10 is a perspective view of the container, and the outer annular container and the inner cylindrical container thereof, of the air freshener of FIG. 1, shown with the cap and the sleeve removed therefrom.
Figure 11:
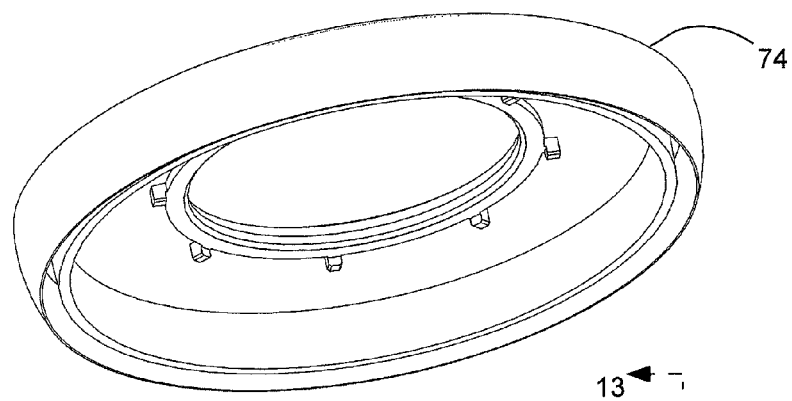
FIG. 11 is a perspective view of the outer annular cap of the air freshener of FIG. 1.
Figure 12:
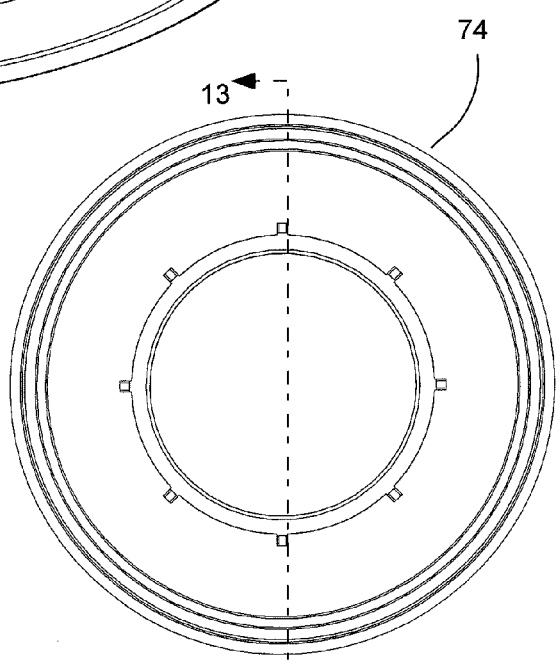
FIG. 12 is a bottom view of the outer annular cap of the air freshener of FIG. 1.
Figure 13:
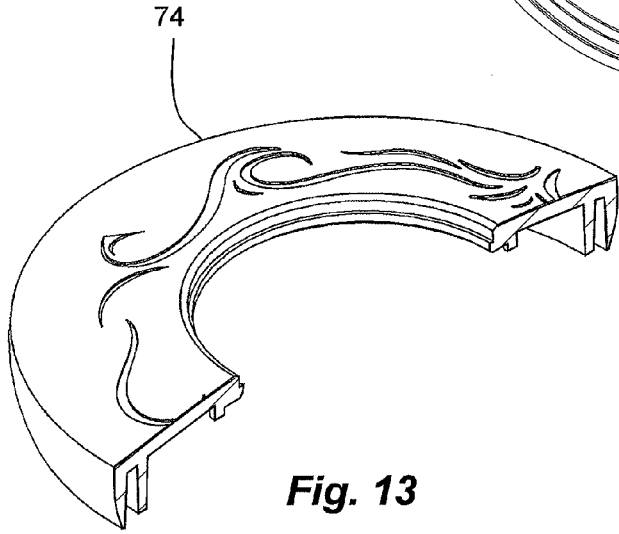
FIG. 13 is a cross-sectional perspective view of the outer annular cap of the air freshener of FIG. 1 taken along line 14 of FIG. 12.

The air freshener 10 also comprises a cap 50 or lid carried by the container 14 and disposable on the container over the open upper end to cover the containers or reservoirs 22 and 26. The cap 50 can be part of the container 14. A sleeve 54 extends from the cap 50 into the container 14, and into the annular gap 38 between the containers or reservoirs 22 and 26, and between the pair of cylindrical walls 30 and 34. The sleeve 54 is cylindrical to match the annular gap and the pair of cylindrical walls 30 and 34. The sleeve 54 can have at least one lateral or radial aperture or opening 58. In one aspect, the at least one aperture 58 can include a plurality of apertures or holes circumscribing the sleeve, and disposed adjacent the top thereof. The cap 50 and the sleeve 54 are movable axially with respect to the container 14 (and thus containers or reservoirs 22 and 26) between a raised position (FIG. 4a) and a closed position (FIG. 4b). In the raised position, the cap and the sleeve, and thus the aperture 58, are raised with respect to the container, and the at least two different fragrances are released. In the raised position, the cap is raised to release the first fragrance from the outer annular container or reservoir, indicated by line 66 in FIG. 4b, and the at least one aperture in the cylindrical sleeve is exposed to release the second fragrance from the inner cylindrical container or reservoir through the aperture, indicated by line 68 in FIG. 4b. In the closed position, the cap covers the container to resist release of the at least two different fragrances, as shown in FIG. 4a. In the closed position, the at least one aperture in the cylindrical sleeve is disposed in the annular gap, and the cap covers the container to resist release of the first and second fragrances.

In one aspect, the cap and the sleeve can extend linearly vertically or axially towards and away from the container, and can be held by a friction resistance or interference fit between the sleeve and the pair of walls. In another aspect, mating screw threads can be formed between the sleeve and the pair of walls such that rotation of the cap moves the cap axially with respect to the container. For example, an inner screw thread 62 can be formed on the inner wall or outermost wall 30 of the outer annular container or reservoir 26. Similarly, an exterior screw thread 64 can be formed on the sleeve 54, and can engaging the interior screw thread 62. The screw threads do not need to be continuous, but can be segmented to form portions of screw threads, such as shown by screw threads 62 in FIG. 5.

The cap 50 and the sleeve 54 can comprise an inverted cup 70 and an outer annular cap 74 coupled together. The inverted cup 70 can have a top wall covering the inner cylindrical container or reservoir 22, and abutting to an upper rim thereof in the closed position. In addition, the inverted cup 70 can have a side wall forming the cylindrical sleeve. The inverted cup 70 can be formed of, or can include, a material that is reactable with the fragrant gel material, such as polystyrene, but is separated from the fragrant gel material by the pair of walls 30 and 34. In another aspect, the inverted cup can be formed of, or can include, a material that resists reacting with the fragrant gel material, such as polypropylene. At least the top wall of the inverted cup, and thus at least a portion of the cap 50 over the inner container or reservoir 22, is transparent, or at least translucent, so that the second fragrant material 18b is visible therethrough. The inverted cup can be translucent or transparent, including the sleeve. The outer annular cap 74 can coupled to the inverted cup 70, and can cover the outer annular container or reservoir 26, and can abut to an upper rim thereof in the closed position. The outer annular cap can have an annular groove or channel formed around a perimeter thereof to receive the upper rim of the outer wall in the closed position. In addition, the outer annular cap can have a center aperture to receive the top wall of the inverted cup. The inverted cup can have a projection extending into the center aperture of the outer annular cap. The outer annular cap and the inverted cup can be adhered together. The outer annular cap can be opaque.

As described above, the outer annular container 26, the inner cylindrical container 22, the cylindrical sleeve 54, and the first fragrant material 18a can be at least translucent so that the second fragrant material 18b is visible laterally therethrough. The outer wall 20 of the outer annular container 26 can be at least translucent, and the first fragrant material 18a can be visible laterally therethrough. At least a portion of the cap 50, such as the top wall of the inverted cup 70, over the inner cylindrical container 22 can be at least translucent so that the second fragrant material 18b is visible axially therethrough.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:
1. An air freshener device, comprising:
 a) an outer annular container having an annular reservoir and containing a first fragrant material from which a first fragrance permeates over time;
 b) the outer annular container having an outer wall and an inner wall;
 c) an inner screw thread formed on the inner wall of the outer annular container;
 d) an inner cylindrical container circumscribed by the outer annular container, and having a cylindrical reservoir containing a second fragrant material from which a different second fragrance permeates over time;
 e) the inner cylindrical container having a wall opposing and spaced apart from the inner wall of the outer annular container, and defining an annular gap therebetween;
 f) a cap carried by the container and covering the reservoirs;
 g) a cylindrical sleeve extending from the cap into the annular gap between the reservoirs;
 h) at least one lateral aperture in the cylindrical sleeve;
 i) an exterior screw thread formed on the sleeve and engaging the interior screw thread on the inner wall of the outer annular container such that rotation of the cap moves the cap axially with respect to the container including a raised position in which the at least one aperture in the cylindrical sleeve is exposed to release the second fragrance from the inner cylindrical container through the at least one aperture in the sleeve, and the cap is raised to release the first fragrance from the outer annular container, and a closed position in which the at least one aperture in the cylindrical sleeve is disposed in the annular gap and the cap covers the container to resist release of the first and second fragrances;
 j) the cap having a top wall covering the inner cylindrical container and abutting to an upper rim thereof in the closed position; and
 k) the cap having an outer annular cap covering outer annular container and abutting to an upper rim thereof in the closed position.
2. The air freshener device in accordance with claim 1, wherein the containers further comprise:
 an interlocking coupling between the containers at a bottom inner rim of the outer annular container, and at a bottom outer rim of the inner cylindrical container.
3. The air freshener device in accordance with claim 1, wherein the outer annular container, the inner cylindrical container, the cylindrical sleeve, and the first fragrant material are at least translucent, and the second fragrant material is visible therethrough.
4. The air freshener device in accordance with claim 1, wherein the outer wall of the outer annular container is at least translucent and the first fragrant material is visible therethrough; and wherein at least a portion of the cap over the inner cylindrical container is at least translucent at the second fragrant material is visible therethrough.
5. An air freshener device, comprising:
 a) a container;
 b) a pair of concentric cylindrical walls disposed in the container and concentric with one another and forming an annular gap therebetween and dividing the container into an inner cylindrical reservoir and an outer annular reservoir circumscribing the inner cylindrical reservoir;

c) a first fragrant material disposed in the outer annular reservoir from which a first fragrance permeates over time;

d) a second fragrant material disposed in the inner cylindrical reservoir from which a different second fragrance permeates over time;

e) a cap carried by the container and covering the reservoirs;

f) a sleeve extending from the cap into the annular gap between the pair of cylindrical walls;

g) at least one opening in the sleeve; and h) the cap movable axially with respect to the container between a raised position in which the at least one opening in the sleeve is exposed at least partially to release the second fragrance from the inner cylindrical reservoir through the at least one opening in the sleeve, and the cap is raised to release the first fragrance from the outer annular reservoir, and a closed position in which the at least one opening in the sleeve is disposed in the annular gap and the cap covers the container to resist release of the first and second fragrances.

6. The air freshener device in accordance with claim 5, further comprising:

mating screw threads formed between the sleeve and at least one of the pair of concentric cylindrical walls such that rotation of the cap moves the cap axially with respect to the container.

7. The air freshener device in accordance with claim 5, wherein the container further comprises:

a) an outer annular container;

b) an inner cylindrical container circumscribed by the outer annular container; and c) an interlocking coupling between the containers at a bottom inner rim of the outer annular container, and at a bottom outer rim of the inner cylindrical container.

8. The air freshener device in accordance with claim 5, wherein the outer annular container, the inner cylindrical container, the cylindrical sleeve, and the first fragrant material are at least translucent, and the second fragrant material is visible therethrough.

9. The air freshener device in accordance with claim 5, wherein an outer wall of the outer annular container is at least translucent and the first fragrant material is visible therethrough; and wherein at least a portion of the cap over the inner cylindrical container is at least translucent at the second fragrant material is visible therethrough.

10. The air freshener device in accordance with claim 5, further comprising:

the cap having a top wall covering the inner cylindrical container and abutting to an upper rim thereof in the closed position; and the cap having an outer annular cap covering the outer annular container and abutting to an upper rim thereof in the closed position.

11. The air freshener device in accordance with claim 10, further comprising:

the outer annular cap having an annular groove formed around a perimeter thereof to receive the upper rim of the outer wall in the closed position.

12. An air freshener device, comprising:

a) a container divided into an inner cylindrical reservoir and an outer annular reservoir being separate and discrete from, and circumscribing, the inner cylindrical reservoir;

b) at least two different fragrant materials with different fragrances that permeate over time, each disposed in a different one of the reservoirs;

c) a cap carried by the container and covering the reservoirs;

d) a sleeve extending from the cap into the container between both of the reservoirs; and e) the cap movable axially with respect to the container between a raised position in which the at least two different fragrances are released, and a closed position in which the cap covers the container to resist release of the at least two different fragrances.

13. The air freshener device in accordance with claim 12, further comprising:

a pair of concentric cylindrical walls disposed in the container and concentric with one another and forming an annular gap therebetween and dividing the container into the inner cylindrical reservoir and the outer annular reservoir.

14. The air freshener device in accordance with claim 13, wherein the sleeve extends from the cap into the annular gap between the pair of cylindrical walls; and wherein the sleeve has at least one opening therethough.

15. The air freshener device in accordance with claim 14, further comprising:

mating screw threads formed between the sleeve and at least one of the pair of concentric cylindrical walls such that rotation of the cap moves the cap axially with respect to the container.

16. The air freshener device in accordance with claim 13, wherein the annular gap is free of fragrant material and has the sleeve movably received therein.

17. The air freshener device in accordance with claim 12, wherein the container further comprises:

a) an outer annular container;

b) an inner cylindrical container circumscribed by the outer annular container; and c) an interlocking coupling between the containers at a bottom inner rim of the outer annular container, and at a bottom outer rim of the inner cylindrical container.

18. The air freshener device in accordance with claim 12, further comprising:

the cap having a top wall covering the inner cylindrical container and abutting to an upper rim thereof in the closed position; and the cap having an outer annular cap covering the outer annular container and abutting to an upper rim thereof in the closed position.

19. The air freshener device in accordance with claim 18, further comprising:

the outer annular cap having an annular groove formed around a perimeter thereof to receive the upper rim of the outer wall in the closed position.

20. The air freshener device in accordance with claim 18, wherein the sleeve extends from the cap between the top wall and the outer annular cap.

* * * * *